United States Patent
Cerini

(10) Patent No.: US 12,251,398 B2
(45) Date of Patent: Mar. 18, 2025

(54) TOPICAL COMPOSITIONS DESIGNATED TO MAINTAIN AND/OR RESTORE THE INTEGRITY OF THE MUCOSA AND DAMAGED EPIDERMIS

(71) Applicant: RICERFARMA S.R.L., Milan (IT)

(72) Inventor: Roberto Cerini, Albignasego (IT)

(73) Assignee: RICERFARMA S.R.L., Milan (IT)

( * ) Notice: Subject to any disclaimer, the term of this patent is extended or adjusted under 35 U.S.C. 154(b) by 0 days.

(21) Appl. No.: 18/477,609

(22) Filed: Sep. 29, 2023

(65) Prior Publication Data

US 2024/0024352 A1 Jan. 25, 2024

Related U.S. Application Data

(63) Continuation of application No. 17/904,957, filed as application No. PCT/IB2021/051573 on Feb. 25, 2021, now abandoned.

(30) Foreign Application Priority Data

Feb. 27, 2020 (IT) ........................ 102020000004069

(51) Int. Cl.
*A61K 31/728* (2006.01)
*A61K 31/341* (2006.01)
*A61K 31/375* (2006.01)
*A61K 31/685* (2006.01)

(52) U.S. Cl.
CPC .......... *A61K 31/728* (2013.01); *A61K 31/341* (2013.01); *A61K 31/375* (2013.01); *A61K 31/685* (2013.01)

(58) Field of Classification Search
CPC ........ A61K 8/416; A61K 8/676; A61K 8/731; A61K 8/735; A61K 8/736; A61K 31/341; A61K 31/385; A61K 31/685; A61K 31/728; A61P 15/02; A61P 17/00–08
See application file for complete search history.

(56) References Cited

U.S. PATENT DOCUMENTS

| | | |
|---|---|---|
| 2007/0196311 A1 | 8/2007 | Gross |
| 2008/0015155 A1 | 1/2008 | Mastrodonato et al. |
| 2008/0188441 A1 | 8/2008 | Reinmuller et al. |
| 2012/0076744 A1 | 3/2012 | Poigny et al. |

FOREIGN PATENT DOCUMENTS

WO 2012073191 A1 6/2012

OTHER PUBLICATIONS

Lee et al., "Quantitative evaluation of mucoadhesive polymers to compare the mucoadhesion" Journal of Pharmaceutical Investigations vol. 46 pp. 189-194, DOI 10. 1007/s40005-016-0233-4 (Year: 2016).*
Palma et al., "Coagels from alkanoyl-6-O-ascorbic acid derivatives as drug carriers: structure and rheology" Il Farmaco vol. 58 pp. 1271-1276, doi: 10.1016/j.farmac.2003.07.010 (Year: 2003).*
Zhang et al., "An inflammation-targeting hydrogel for local drug delivery in inflammatory bowel disease" Science Translational Medicine vol. 7 issue 300 pp. 1-10 (Year: 2015).*
Garca A et al, "Useful in vitro technique to evaluate the mucoadhesive properties" Pharmaceutics, vol. 10, pp. 1-16, 2018.
International Preliminary Report on Patentability of PCT/IB2021/051573 issued Jan. 19, 2022.
Search Report and Written Opinion of PCT/IB2021/051573 of Jun. 16, 2021.
Tomohara K et al., "Interpreting the behavior of concentration-response curves of hyaluronidase inhibitors under DMSO-perturbed assay conditions", Bioorg. Med. Chem. Lett. 26(2016) 3153-3157.

\* cited by examiner

*Primary Examiner* — Eric Olson
(74) *Attorney, Agent, or Firm* — Silvia Salvadori, P.C.; Silvia Salvadori

(57) ABSTRACT

Disclosed are topical mucoadhesive compositions comprising hyaluronic acid or a salt thereof, choline alfoscerate, an ascorbic acid ester at a concentration ranging between 0.050% w/w and 0.0004% w/w, and at least one pharmaceutically acceptable excipient or carrier.

8 Claims, No Drawings

TOPICAL COMPOSITIONS DESIGNATED TO MAINTAIN AND/OR RESTORE THE INTEGRITY OF THE MUCOSA AND DAMAGED EPIDERMIS

This non-provisional application is a continuation of U.S. Ser. No. 17/904,957, which is a U.S. national stage of PCT/IB2021/051573 filed on 25 Feb. 2021, which claims priority to and the benefit of Italian Patent Application No. 102020000004069 filed on 27 Feb. 2020, the contents of which are incorporated herein by reference in their entireties.

The invention relates to topical compositions for the maintenance and/or restoration of the integrity of the damaged mucous membranes and epidermis.

PRIOR ART

The integrity of the skin tissue and mucous membranes can be affected by a variety of exogenous and endogenous causes, such as vitamin deficiencies, incorrect diet, poor hygiene, bacterial, viral or fungal infections, intestinal dysbiosis, alterations of the mucosal microbial flora, endocrine imbalances, debilitating diseases, hereditary factors, mechanical, physical, chemical and traumatic factors, radiation, etc.

EP2646036 discloses compositions useful to maintain and restore the integrity of the mucous membranes and epidermis, comprising choline alfoscerate and hyaluronic acid.

Choline alfoscerate is known as a nootropic substance able to improve the trophism of the brain cells (by activating the blood supply and cell metabolism), and consequently the intellectual functions. WO93/19730 discloses its use on the skin and hair with a moisturising, emollient, elasticising, restorative, volume-enhancing action.

As disclosed in WO93/19730, choline alfoscerate is practically devoid of systemic toxicity, and has marked topical tolerability. It is known in the pharmaceutical field for its use in injectable compositions and oral compositions for the treatment of alterations of the cognitive functions, and as a possible growth hormone secreting factor.

Hyaluronic acid, which is widely present in various human and animal body tissues, possesses high viscoelasticity and the ability to retain up to 1000 times its weight in water. It is widely used, mainly in the form of sodium hyaluronate, in cosmetic and pharmaceutical formulations, for its mucoadhesive, anti-inflammatory and reparatory properties.

Ascorbyl palmitate (AP), a liposolubile form of vitamin C, is useful to protect lipids from peroxidation, and is mainly used in cosmetics at concentrations ranging between 1.0 and 0.1% w/w for antioxidant and antiradical purposes in anti-aging treatments. Similarly to lipids it easily penetrates the skin and mucous membranes, wherein it exerts an antioxidant action, preventing cell aging and collagen degeneration. Ascorbyl palmitate is also sold in the form of a diet supplement, to promote iron absorption, assist blood circulation and enhance collagen formation, thereby helping to avoid the onset of joint pain and rheumatism. It is also used as a food additive (E304) for antioxidant purposes. It is also known that ascorbic acid and the esters thereof, in particular L-ascorbyl palmitate, has significant inhibitory activity against hyaluronidases, the enzymes responsible for the degradation of hyaluronic acid.

The need is particularly felt for compositions which are useful to maintain and restore the integrity of the mucous membranes and adaptable to various types of formulation for different application sites, and have synergic effects between the ingredients and improved stability towards hyaluronidases.

DESCRIPTION OF THE INVENTION

It has now been found that topical use on the damaged mucous membranes and epidermis of a combination of high-molecular-weight hyaluronic acid, an ascorbic acid ester, preferably ascorbyl palmitate, in concentrations lower than or equal to 0.05% w/w, and choline alfoscerate in a bio/mucoadhesive matrix, maintains and restores the integrity of the mucosal and epidermal tissue with an efficacy and flexibility of application superior to those of the known formulations.

The combination of the invention is particularly useful for the treatment of irritative/inflammatory conditions of the damaged mucous membranes and epidermis (burns, sores, heat rash, dermatitis and the like).

The invention therefore provides topical mucoadhesive compositions comprising hyaluronic acid or a salt thereof, choline alfoscerate, an ascorbic acid ester at a concentration ranging between 0.050% w/w and 0.0004% w/w, and at least one pharmaceutically acceptable excipient or carrier.

The ascorbic acid ester, preferably ascorbyl palmitate, is present in the formulations of the invention in concentrations lower than those usually employed for use as an anti-oxidant and anti-radical agent (0.500-0.100% w/w) in conventional cosmetic and dermatological formulations.

The best balance between the anti-hyaluronidase efficacy and mucoadhesive properties of the formulations is considered to be achieved at the indicated concentrations of ascorbic acid ester.

The average molecular weight of hyaluronic acid preferably ranges between 800,000 and 4,000,000 Da. Hyaluronic acid can be present in the formulations in the form of sodium salt at concentrations ranging between 20.000% w/w and 0.0005% w/w.

Choline alfoscerate is present in concentrations ranging from 0.0005 to 10.000% w/w, preferably from 0.001% to 1.000% w/w.

The compositions of the invention also contain one or more mucoadhesive agents selected from beta-glucan, sodium carboxymethyl beta-glucan, chitosan, carboxymethyl chitosan, carboxymethylcellulose, hydroxyethylcellulose, carbomer, PVA (polyvinyl alcohol), PVP (polyvinylpyrrolidone), polycarbophil (polyacrylic acid crosslinked with divinyl glycol), PVM/MA copolymer (copolymer of methyl vinyl ether and maleic anhydride) and VP/eicosene copolymer (1-vinyl-2-pyrrolidinone-1-eicosene (1:1)).

According to a further aspect, the compositions of the invention can also include further active ingredients useful for topical treatment of the mucous membranes, such as those described in Martindale, The Complete Drug Reference, 34th Edition.

The compositions of the invention can be formulated in a way suitable for topical administration according to well-known conventional methods, such as those described in Remington, The Science and Practice of Pharmacy, 20th Edition.

Known excipients or carriers, such as film-forming agents, like those described in Handbook of Pharmaceutical Excipients, 6th Edition, Pharmaceutical Press, can also be added to optimise the specific use of the compositions.

Examples of preferred formulations are gels, oil in water (o/w) and water-in-oil (w/o) emulsions, creams, ointments, sprays, powders, lotions and foams.

Particularly preferred compositions are in aqueous gel form (hydrogel), which can be obtained by using a pharmaceutically acceptable polymer able to absorb a considerable amount of water and thus adhere to the mucous membranes (mucoadhesion).

The mucoadhesion of the compositions of the invention ensures an adequate residence time on the mucous membranes, which is subject to the leaching action of physical and mechanical factors that can reduce the residence time of the active ingredient, for example in the case of the oral mucous membranes.

The compositions according to the invention, which are suitable for human or veterinary use, combine the anti-inflammatory and tissue repair action of hyaluronic acid with the film-forming and protective action of bio/mucoadhesive formulation matrices containing choline alfoscerate and the anti-hyaluronidase action of ascorbyl palmitate at low concentrations.

In the preferred embodiments, hyaluronic acid and ascorbic acid ester, preferably ascorbyl palmitate, are in a molar ratio (relative to the disaccharide unit of hyaluronic acid) ranging from 60:1 to 1:1. More preferably, hyaluronic acid and ascorbic acid ester are in a molar ratio ranging from 20:1 to 1:1; the best anti-hyaluronidase activity is obtained in said proportions.

In fact, in the presence of hyaluronidase, hyaluronic acid degrades rapidly by up to 95-97% after only 5 hours. As will be seen in the Examples below, ascorbyl palmitate has proved to be significantly effective in slowing enzymatic kinetics and consequently in reducing the undesirable degradation of hyaluronic acid. In fact, after 5 h, the compositions containing ascorbyl palmitate exhibited up to 50% less HA degradation than observed in samples of hyaluronic acid used alone or combined with choline alfoscerate. After 24 h, the compositions containing ascorbyl palmitate exhibited up to 27% less HA degradation than observed in samples of hyaluronic acid used alone or combined with choline alfoscerate.

The anti-hyaluronidase activity of ascorbyl palmitate synergises with the action of hyaluronic acid, whether endogenous to the tissue or exogenous. Anti-hyaluronidase action is of crucial importance to increase the anti-inflammatory and tissue repair efficacy of hyaluronic acid, protecting it against the enzymatic action of endogenous and bacterial hyaluronidase and guaranteeing lengthy functional residence in situ, and therefore greater efficacy combined with greater bioavailability and structural integrity.

Moreover, the anti-hyaluronidase action also performs an antibacterial/anti-inflammatory action; in fact, many bacteria perform an inflammatory action by producing specific hyaluronidases which promote tissue colonisation, thereby promoting the onset and spread of bacterial infections/contamination at local level.

On the basis of the considerations set out above, the anti-inflammatory/tissue repair action of HA is protected and strongly enhanced by the anti-hyaluronidase action and the presence of the film-forming and bio/mucoadhesive matrix able to form a favourable environment for tissue protection and repair (wound-healing).

The compositions of the invention can be applied to the external mucous membranes, such as the mucous membranes of the mouth and the oral cavity in general, nasal mucous membranes, ocular mucous membranes, aural mucous membranes, genital mucous membranes, anal and rectal mucous membranes.

The compositions of the invention are useful in the prevention and treatment of inflammatory disorders and/or those involving damage to the oral mucous membranes, in the prevention and/or treatment of damaged and/or inflamed gums, and in the treatment of radiation-induced mucositis.

Inflammation and lesions of the oral mucous membranes means, for example, gingivitis, mucositis (mouth ulcers, including recurrent mouth ulcers), stomatitis, glossitis, etc. These disorders can have different etiologies; for example, they can have mechanical, chemical or pathological causes (infections, dysbiosis of the oral cavity or intestinal dysbiosis).

The examples below further illustrate the invention. The percentages are expressed as parts by weight (w/w) of the total volume of the composition.

Example 1—Liquid Composition for Oral Mucous Membranes

| Compound | Percentage |
| --- | --- |
| Choline alfoscerate | 1.000% |
| Sodium hyaluronate (mean MW 1,500,000 Da) | 0.300% |
| Ascorbyl palmitate | 0.005% |
| Polycarbophil | 0.050% |
| Carboxymethyl chitosan | 0.100% |
| PVP (polyvinylpyrrolidone) | 0.500% |
| Solubilising agent | q.s. |
| Preservative | q.s. |
| Flavouring | q.s. |
| Demineralised water | q.s. to 100% |

Example 2—Gel Composition for Treatment of Mouth Ulcers

| Compound | Percentage |
| --- | --- |
| Sodium hyaluronate (mean MW 1,500,000 Da) | 0.400% |
| Ascorbyl palmitate | 0.040% |
| Choline alfoscerate | 0.200% |
| Carboxymethylcellulose | 1.000% |
| Polycarbophil | 0.500% |
| PVP (polyvinylpyrrolidone) | 1.000% |
| PVA (polyvinyl alcohol) | 0.500% |
| Xylitol | 7.000% |
| Solubilising agent | q.s. |
| Preservative | q.s. |
| Flavouring | q.s. |
| Demineralised water | q.s. to 100% |

Example 3—Gel Composition for Treatment of Oral Mucositis

| Compound | Percentage |
| --- | --- |
| Sodium hyaluronate (mean MW 1,500,000 Da) | 0.500% |
| Ascorbyl palmitate | 0.050% |
| Choline alfoscerate | 0.100% |
| Carboxymethylcellulose | 1.000% |
| Polycarbophil | 0.400% |
| Carboxymethyl chitosan | 0.150% |
| PVP (polyvinylpyrrolidone) | 1.500% |
| PVA (polyvinyl alcohol) | 0.500% |
| Xylitol | 7.500% |
| Solubilising agent | q.s. |
| Preservative | q.s. |
| Flavouring | q.s. |
| Demineralised water | q.s. to 100% |

Example 4—Liquid Composition for Treatment of Oral Mucositis

| Compound | Percentage |
| --- | --- |
| Sodium hyaluronate (mean MW 1,500,000 Da) | 0.200% |
| Ascorbyl palmitate | 0.020% |
| Choline alfoscerate | 0.050% |
| Polycarbophil | 0.050% |
| Carboxymethyl chitosan | 0.050% |
| PVP (polyvinylpyrrolidone) | 0.200% |
| PVA (polyvinyl alcohol) | 0.100% |
| Xylitol | 7.500% |
| Solubilising agent | q.s. |
| Preservative | q.s. |
| Flavouring | q.s. |
| Demineralised water | q.s. to 100% |

Example 5—Gel Composition for Use on the Nasal Mucous Membranes

| Compound | Percentage |
| --- | --- |
| Choline alfoscerate | 0.050% |
| Sodium hyaluronate (mean MW 1,500,000 Da) | 0.200% |
| Ascorbyl palmitate | 0.020% |
| Carboxymethylcellulose | 4.500% |
| Polycarbophil | 0.300% |
| PVM/MA Copolymer | 0.150% |
| PVP (polyvinylpyrrolidone) | 0.500% |
| PVA (polyvinyl alcohol) | 0.100% |
| Distilled *Euphrasia* water | 10.000% |
| Sodium chloride | 0.800% |
| Dibasic sodium phosphate dodecahydrate | 0.300% |
| Monobasic sodium phosphate monohydrate | 0.030% |
| Solubilising agent | q.s. |
| Preservative | q.s. |
| Demineralised water | q.s. to 100% |

Example 6—Liquid Composition for Use on the Ocular Mucous Membranes

| Compound | Percentage |
| --- | --- |
| Choline alfoscerate | 0.010% |
| Sodium hyaluronate (mean MW 1,500,000 Da) | 0.150% |
| Ascorbyl palmitate | 0.005% |
| Polycarbophil | 0.050% |
| Carboxymethyl chitosan | 0.050% |
| Distilled witch hazel water | 10.000% |
| Distilled camomile water | 10.000% |
| Sodium chloride | 0.800% |
| Dibasic sodium phosphate dodecahydrate | 0.300% |
| Monobasic sodium phosphate monohydrate | 0.030% |
| EDTA | 0.050% |
| Demineralised water | q.s. to 100% |

Example 7—Liquid Composition for Use on the Aural Mucous Membranes

| Compound | Percentage |
| --- | --- |
| Choline alfoscerate | 0.100% |
| Sodium hyaluronate (mean MW 1,500,000 Da) | 0.100% |
| Ascorbyl palmitate | 0.015% |
| Polycarbophil | 0.050% |
| PVM/MA copolymer | 0.150% |
| Glycerol | 50.000% |
| Demineralised water | q.s. to 100% |

Example 8—Liquid Composition for Use on the Vaginal and Vulvar Mucous Membranes

| Compound | Percentage |
| --- | --- |
| Choline alfoscerate | 0.050% |
| Sodium hyaluronate (mean MW 1,500,000 Da) | 0.200% |
| Ascorbyl palmitate | 0.010% |
| Polycarbophil | 0.100% |
| PVM/MA Copolymer | 0.050% |
| PVP (polyvinylpyrrolidone) | 0.200% |
| PVA (polyvinyl alcohol) | 0.100% |
| Sodium chloride | 0.800% |
| Preservative | q.s. |
| Perfume | q.s. |
| Demineralised water | q.s. to 100% |

Example 9—Gel Composition for Use on the Vaginal and Vulvar Mucous Membranes

| Compound | Percentage |
| --- | --- |
| Choline alfoscerate | 0.025% |
| Sodium hyaluronate (mean MW 1,500,000 Da) | 0.150% |
| Ascorbyl palmitate | 0.040% |
| Carboxymethylcellulose sodium salt | 4.500% |
| Polycarbophil | 0.250% |
| PVM/MA copolymer | 0.150% |
| PVP (polyvinylpyrrolidone) | 0.500% |
| PVA (polyvinyl alcohol) | 0.100% |
| Sodium chloride | 0.800% |
| Solubilising agent | q.s. |
| Preservative | q.s. |
| Perfume | q.s. |
| Demineralised water | q.s. to 100% |

Example 10—Gel Composition for Use on the Mucous Membranes of the Male Genitals

| Compound | Percentage |
| --- | --- |
| Choline alfoscerate | 0.500% |
| Sodium hyaluronate (mean MW 1,500,000 Da) | 0.250% |
| Ascorbyl palmitate | 0.050% |
| Carboxymethylcellulose sodium salt | 4.500% |
| Polycarbophil | 0.250% |
| PVM/MA Copolymer | 0.150% |
| PVP (polyvinylpyrrolidone) | 0.500% |
| PVA (polyvinyl alcohol) | 0.100% |
| Sodium chloride | 0.800% |
| Solubilising agent | q.s. |
| Preservative | q.s. |
| Demineralised water | q.s. to 100% |

Example 11—Gel Composition for Use on the Anorectal Mucous Membranes

| Compound | Percentage |
| --- | --- |
| Choline alfoscerate | 0.500% |
| Sodium hyaluronate (mean MW 1,500,000 Da) | 0.250% |
| Ascorbyl palmitate | 0.015% |
| Carboxymethylcellulose sodium salt | 4.500% |
| Polycarbophil | 0.250% |
| Carboxymethyl chitosan | 0.150% |
| PVM/MA copolymer | 0.150% |
| PVP (polyvinylpyrrolidone) | 0.500% |
| PVA (polyvinyl alcohol) | 0.100% |
| Distilled white thyme water | 10.000% |
| Distilled lavender water | 10.000% |
| Distilled cornflower water | 10.000% |
| Sodium chloride | 0.800% |
| Solubilising agent | q.s. |
| Preservative | q.s. |
| Demineralised water | q.s. to 100% |

Example 12—Gel Composition for the Treatment of Inflamed Gums

| Compound | Percentage |
| --- | --- |
| Choline alfoscerate | 0.250% |
| Sodium hyaluronate (mean MW 1,500,000 Da) | 0.450% |
| Ascorbyl palmitate | 0.045% |
| Xylitol | 7.500% |
| Carboxymethylcellulose sodium salt | 4.000% |
| Polyvinyl alcohol | 0.300% |
| Polycarbophil | 0.300% |
| VP/eicosene copolymer | 0.100% |
| PVM/MA copolymer | 0.150% |
| PVP (polyvinylpyrrolidone) | 0.500% |
| Solubilising agent | q.s. |
| Preservative | q.s. |
| Flavouring | q.s. |
| Colouring | q.s. |
| Demineralised water | q.s. to 100% |

Example 13—Gel Composition for the Treatment of Damaged Gums

| Compound | Percentage |
| --- | --- |
| Choline alfoscerate | 0.500% |
| Sodium hyaluronate (mean MW 1,500,000 Da) | 0.350% |
| Ascorbyl palmitate | 0.025% |
| Xylitol | 7.500% |
| Carboxymethylcellulose sodium salt | 4.000% |
| Polyvinyl alcohol | 0.100% |
| Polycarbophil | 0.100% |
| VP/eicosene copolymer | 0.100% |
| PVM/MA copolymer | 0.150% |
| PVP (polyvinylpyrrolidone) | 0.500% |
| Solubilising agent | q.s. |
| Preservative | q.s. |
| Flavouring | q.s. |
| Colouring | q.s. |
| Demineralised water | q.s. to 100 |

Example 14—Vaginal Pessary

| Compound | Percentage |
| --- | --- |
| Choline alfoscerate | 0.100% |
| Sodium hyaluronate (mean MW 1,500,000 Da) | 0.200% |
| Ascorbyl palmitate | 0.045% |
| Carboxymethyl chitosan | 0.050% |
| Carboxymethyl beta glucan | 0.050% |
| Gelatin | 20.000% |
| Glycerol | 70.000% |
| Demineralised water | q.s. to 100% |

Example 15—Anorectal Enema Composition

| Compound | Percentage |
| --- | --- |
| Choline alfoscerate | 0.300% |
| Sodium hyaluronate (mean MW 1,500,000 Da) | 0.300% |
| Ascorbyl palmitate | 0.050% |
| Colloidal silicon dioxide | 1.700% |
| Polyvinylpyrrolidone | 0.840% |
| Carboxymethylcellulose | 0.840% |
| Polycarbophil | 0.100% |
| Carboxymethyl chitosan | 0.050% |
| Sodium benzoate | 0.400% |
| Potassium metabisulphite | 0.250% |
| Phosphoric acid | 0.100% |
| Demineralised water | q.s. to 100 |

Example 16. Study of Hyaluronic Acid Enzymatic Degradation in Formulations Containing Glycerophosphocholine and Ascorbyl Palmitate The aim of this work has been the evaluation of the enzymatic degradation of two different batches of Hyaluronic Acids (HA) operated by Hyaluronidase, family of enzymes that catalyze the degradation of this polysaccharide, in formulations containing different ingredients. The molecular weight distribution of degraded acids will be analyzed by using High Performance Size Exclusion Chromatography coupled with a Triple Detector Array (HP-SEC-TDA).

The following is the list of reagents and materials used:
Hyaluronic acid (Mw 1.348.000 Da), Contipro a.s. (Czech Republic)
Hyaluronic acid (Mw 1.450.000 Da), Lehvoss Italia S.r.l. (Italy)
Glycerophosphocholine
Ascorbyl Palmitate
Citric acid monohydrate, Sigma Aldrich
Deionized H2O obtained with a Culligan apparatus;
Hyaluronidase from bovine testes I-S Type. 400-1000 units/mg. Sigma Aldrich;
NaNO3. Sigma Aldrich;
NaN3. Sigma Aldrich;
Snap-it vial 0.3 ml, 11.6×32 mm. Thermo Scientific;
Snap-it cap 11 mm, Thermo Scientific;
Sodium citrate diidrate, Sigma Aldrich.

Samples Prepared and Tested:
HA Contipro (solution A): about 50 mg of HA sample were dissolved in 50 ml of citrate buffer (pH=6.06) and stirred for 16 hours at 38° C.; the concentration of the Hyaluronic Acid solution is about 1 mg/ml. 10 ml of solution were hydrolyzed.

HA Levhoss (solution B): about 50 mg of HA sample were dissolved in 50 ml of citrate buffer (pH=6.06) and stirred for 16 hours at 38° C.; the concentration of the Hyaluronic Acid solution is about 1 mg/ml. 10 ml of solution were hydrolyzed.

HA Contipro+GPC (solution C): 7.5 mg of Glycerophosphocholine were added to 10 ml of solution A.

HA Levhoss+GPC (solution D): 7.5 mg of Glycerophosphocholine were added to 10 ml of solution B.

HA Contipro+GPC+AP (solution E): 5 mg of Ascorbyl Palmitate and 7.5 mg of Glycerophosphocholine were added to 10 ml of solution A.

HA Levhoss+GPC+AP (solution F): 5 mg of Ascorbyl Palmitate and 7.5 mg of Glycerophosphocholine were added to 10 ml of solution B.

Buffer Solution Preparation:

Solution 1: 420 mg of citric acid monohydrate were dissolved in 100 ml of deionized water at room temperature for 30'.

Solution 2: 9.212 g of sodium citrate dihydrate were dissolved in 100 ml of deionized water at room temperature for 30'.

Buffer Solution: Solution 1 has been added to Solution 2 and stirred at room temperature for 30'. Resulting pH=6.06.

Enzyme Solution Preparation:

Hyaluronidase: about 10 mg of hyaluronidase were dissolved in about 1 ml of $H_2O$ and stirred at room temperature for 3 hours (10 mg/ml).

Enzymatic Degradation Procedure:

The solutions were stirred at 38° C. in an oil bath for about 1 h before adding 67 μl of the enzyme solution (HA/Hyaluronidase 15/1 w/w).

Different aliquots of solutions were collected at different timing (1 h; 2 h; 3 h; 4 h; 5 h; 6 h, 24 h) and heated at 100° C. for 5' using a thermoshaker to denature the enzyme. The solutions were filtrated to remove the precipitated enzyme (LLG-Syringe filter CA pore size 0.20 μm. Ø 13 mm). Before HP-SEC-TDA analyses, the solutions were diluted to 0.5 mg/ml of HA with mobile phase.

HP-SEC-TDA Analysis
Chromatographic Conditions

Two equivalent HP-SEC-TDA instruments were used:
1) Viscotek system model TDA305. equipped with Refractive Index, Right and Low Angle Light Scattering and Viscometers detectors, was used under the following conditions:
Columns: 2 columns TSKGMPWXL 13 μm. 7 mm ID×30 cm L. Tosoh Bioscience;
Mobile phase: 0.1 M $NaNO_3$+$NaN_3$ 0.05%;
Injection volume: 100 μl;
Temperature: 40° C.;
Flow rate: 0.6 ml/min.
2) OmniSEC Multi-detector System (Malvern Instruments Ltd. UK) equipped with Refractive Index, Right and Low Angle Light Scattering and Viscometers detectors, was used under the following conditions:
Columns: 2 columns TSKGMPWXL 13 μm. 7 mm ID×30 cm L. Tosoh Bioscience;
Mobile phase: 0.1 M $NaNO3$+$NaN3$ 0.05%;
Injection volume: 100 μl;
Temperature: 40° C.;
Flow rate: 0.6 ml/min.

The systems were calibrated with Pullulan standard, with molecular weight. polydispersity index and intrinsic viscosity certified (PolyCAL-PullulanSTD-Malvern Panalytical).

Chromatogram Elaboration

Chromatograms from the TDA 305 were acquired and elaborated using OmniSEC software version 4.6.2. whereas chromatograms from the OmniSEC Multi-detector System were acquired and elaborated using OmniSEC software version 10.10.

Results

Molecular Weight Distribution Evaluation

Starting Sample Preparation

About 50 mg Hyaluronic Acid were dissolved in 50 ml of Citrate buffer, stirred for 16 h, diluted to 0.5 mg/ml with mobile phase and injected once. To evaluate the molecular weight distribution of Hyaluronic acid, 0.155 dn/dc value was used known by literature (ref Theisen A. Johann C. Deacon MP. Harding SE. Refractive Increment Data-Book. Nottingham University Press. 2000).

HA sample has an elution time between 10 and 15 ml with a large bell-shape chromatographic peak. index of a quite high polydispersion index value. After HA peak, the mobile phase profiles are eluted.

In Table 1. the analysis results are reported in terms of weight-average molecular weight (Mw Da), number-average molecular weight (Mn. Da), peak molecular weight (Mp. Da), and polydispersion index (Mw/Mn); further over, thanks to TDA technique, intrinsic viscosity value ([η], dl/g). hydrodynamic radius (Rh, nm) and Recovery %. The values of a and log k which represent respectively the slope and intercept constants of the Mark-Houwink curve are also reported; the results are a mean of two different analysis and the values of Mn and Mw are rounded to the thousands Da.

TABLE 1

HP-SEC-TDA HA results of HA samples

| Sample | Mn (Da) | Mw (Da) | Mw/Mn | MH α | MH logk | [η] dl/g | Rh (nm) | Recovery % |
|---|---|---|---|---|---|---|---|---|
| HA Contipro | 1,034 kDa | 1,348 kDa | 1.3 | 0.65 | −2.68 | 19.32 | 72.72 | 84.38 |
| HA Lehvoss | 1,097 kDa | 1,450 kDa | 1.32 | 0.66 | −2.74 | 20.07 | 75.49 | 81.72 |

Enzymatic Hydrolysis Samples

Hyaluronidase action over Hyaluronic acids have been widely studied and reported; in order to study the enzymatic activity of hyaluronidase on the samples prepared, the kinetics of the hydrolysis were monitored by HP-SEC-TDA technique. The percentual decrease of the molecular weight (in terms of $M_w$) of the polysaccharide's component was determined by using the following formula:

$$((Mwt0-Mwtn)*100)/Mwt0$$

where Mwt0 is the weight-average molecular weight ($M_w$) at time 0 and $M_w$tn is the $M_w$ at time n.

HP-SEC-TDA HA Degradation with Hyaluronidase

The samples have been hydrolyzed twice, to verify the reproducibility. In the tables below, the average values of the molecular weight (rounded to the hundreds) and the corresponding percentual decreases of both experiments are reported.

TABLE 2

HP-SEC-TDA HA degradation (solution A)

| Time | $M_w$ (Da) | % decrease of $M_w$ |
|---|---|---|
| 0 | 1,348,000 | 0 |
| 1 h | 267,700 | 63% |
| 2 h | 140,850 | 90% |
| 3 h | 104,000 | 92% |
| 4 h | 76,610 | 94% |
| 5 h | 64,590 | 95% |
| 17 h | 23,620 | 98% |
| 24 h | 23,920 | 98% |

TABLE 3

HP-SEC-TDA HA degradation (solution B)

| Time | $M_w$ (Da) | % decrease of $M_w$ |
|---|---|---|
| 0 | 1,450,000 | 0 |
| 1 h | 213,500 | 86% |
| 2 h | 107,595 | 93% |
| 3 h | 74,920 | 95% |
| 4 h | 59,620 | 96% |
| 5 h | 50,480 | 97% |
| 17 h | 18,200 | 99% |
| 24 h | 24,980 | 98% |

TABLE 4

HP-SEC-TDA HA degradation (solution C)

| Time | $M_w$ (Da) | % decrease of $M_w$ |
|---|---|---|
| 0 | 1,348,000 | 0% |
| 1 h | 269,500 | 80% |
| 2 h | 169,200 | 87% |
| 3 h | 95,840 | 93% |
| 4 h | 92,710 | 93% |
| 5 h | 85,790 | 94% |
| 24 h | 29,100 | 98% |

TABLE 5

HP-SEC-TDA HA degradation (solution D)

| Time | $M_w$ (Da) | % decrease of $M_w$ |
|---|---|---|
| 0 | 1,450,000 | 0 |
| 1 h | 191,500 | 87% |
| 2 h | 117,300 | 92% |
| 3 h | 59,680 | 96% |
| 4 h | 54,650 | 96% |
| 5 h | 52,880 | 96% |
| 24 h | 16,790 | 99% |

TABLE 6

HP-SEC-TDA HA degradation (solution E)

| Time | $M_w$ (Da) | % decrease of $M_w$ |
|---|---|---|
| 0 | 1,348,000 | 0% |
| 1 h | 716,200 | 47% |
| 3 h | 698,900 | 48% |
| 5 h | 692,100 | 49% |
| 20 h | 394,500 | 71% |
| 24 h | 382,000 | 72% |

TABLE 7

HP-SEC-TDA HA degradation (solution F)

| Time | $M_w$ (Da) | % decrease of $M_w$ |
|---|---|---|
| 0 | 1,450,000 | 0% |
| 1 h | 571,100 | 61% |
| 3 h | 556,700 | 62% |
| 5 h | 552,000 | 62% |
| 20 h | 344,300 | 76% |
| 24 h | 336,400 | 77% |

CONCLUSIONS

Both Hyaluronic Acid samples as such, in presence of Hyaluronidase, are rapidly degraded up to 95-97% in 5 h. Lehvoss Hyaluronic acid is degraded slightly faster than Contipro hyaluronic acid, even if after 24 h the decrease of Mw is quite the same.

Glycerophosphocholine does not contribute in any way to the enzymatic kinetics, as shown by the results of solutions C and D.

Conversely, the addition of Ascorbyl Palmitate has shown to be significantly effective in slowing down the enzymatic kinetics and reducing the undesired HA degradation.

Indeed, after 5 h, all the solutions A to D have shown a HA degradation of up to 97%, whereas solutions E and F featuring ascorbyl palmitate have shown a HA degradation of 49% and 62%, respectively (consistently with the different degradation rates observed for the HA products as such, i.e. solution A and solution B). This means an improvement over the solutions without ascorbyl palmitate, up to 50%.

After 24 h, solutions E and F featuring ascorbyl palmitate have shown a HA degradation of 72% and 77%, respectively. This means an improvement over the solutions without ascorbyl palmitate, up to 27%.

The invention claimed is:

1. A topical mucoadhesive composition comprising hyaluronic acid or a salt thereof, choline alfoscerate, ascorbyl palmitate at a concentration ranging between 0.050% w/w and 0.0004% w/w, and at least one pharmaceutically acceptable excipient or carrier.

2. The composition according to claim 1 wherein the hyaluronic acid or a pharmaceutically acceptable salt thereof has a molecular weight ranging from 800,000 to 4,000,000 Da.

3. The composition according to claim 2, wherein the hyaluronic acid is in the form of sodium salt at a concentration ranging from 20.000% w/w to 0.0005% w/w.

4. The composition according to claim 1 wherein the concentration of choline alfoscerate is between 0.0005% w/w and 10.000% w/w.

5. The composition according to claim 1 wherein the pharmaceutically acceptable excipient or carrier is selected from beta-glucan, sodium carboxymethyl beta-glucan, chitosan, carboxymethyl chitosan, carboxymethylcellulose, hydroxyethylcellulose, carbomer, polyvinyl alcohol, polyvinylpyrrolidone, polycarbophil, PVM/MA copolymer (copolymer of methyl vinyl ether and maleic anhydride) and VP/eicosene copolymer (1-vinyl-2-pyrrolidinone-1-eicosene (1:1)).

6. The composition according to claim 1 in the form of hydrogels, lipogels, anhydrous gels, O/W or W/O emulsions, solutions or suspensions.

7. A method of maintaining and restoring integrity of mucous membranes and skin and preventing and treating inflammatory diseases affecting them with the composition of claim 1 in subjects in need thereof, said method comprising applying said compositions to said mucous membranes and skin of said subjects; and maintaining and restoring said integrity of said mucous membranes and skin and preventing and treating said inflammatory diseases affecting them.

8. The method according to claim 7 wherein the mucous membranes comprise the oral, gingival, nasal, ocular, aural, vaginal, vulvar, anorectal and genital mucosa.

* * * * *